US00PP37664P2

(12) United States Plant Patent
Nebelmeir

(10) Patent No.: US PP37,664 P2
(45) Date of Patent: Sep. 1, 2026

(54) POINSETTIA PLANT NAMED 'LAZZPOGENA'

(50) Latin Name: ***Euphorbia pulcherrima* Willd.**
Varietal Denomination: LAZZPOGENA

(71) Applicant: LAZZERI GENETICA S.A.S. di DALLAGO FRANCO & C., Merano (IT)

(72) Inventor: Johannes Nebelmeir, Hann. Munden (DE)

(73) Assignee: LAZZERI GENETICA S.A.S. di DALLAGO FRANCO & C., Merano (IT)

( * ) Notice: Subject to any disclaimer, the term of this patent is extended or adjusted under 35 U.S.C. 154(b) by 0 days.

(21) Appl. No.: 19/352,112

(22) Filed: Oct. 7, 2025

(51) Int. Cl.
*A01H 6/38* (2018.01)
*A01H 5/02* (2018.01)

(52) U.S. Cl.
USPC ..... Plt./303

(58) Field of Classification Search
USPC ..... Plt./303
CPC ..... A01H 6/38; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of Poinsettia plant named 'LAZZPOGENA', characterized by its upright and broad "V"-shaped and uniformly mounding plant habit; moderately vigorous growth habit; short internodes; freely branching habit and strong stems; dark green-colored leaves; full inflorescences with pale yellow and purplish pink bi-colored flower bracts; and excellent post-production longevity.

1 Drawing Sheet

Botanical designation: *Euphorbia pulcherrima* Willd.
Cultivar denomination: 'LAZZPOGENA'.

CROSS-REFERENCED TO CLOSELY-RELATED APPLICATIONS

A European Community Plant Breeder's Rights application for the instant plant was filed by the Applicant/Assignee of the instant application, Lazzeri Genetica S.A.S. di Dallago Franco & C. of Merano, Italy on Sep. 29, 2025, application number 2025/2053. Foreign priority is not claimed to this application.

BACKGROUND OF THE INVENTION

The present invention relates to a new and distinct cultivar of Poinsettia plant, botanically known as *Euphorbia pulcherrima* Willd. and hereinafter referred to by the name 'LAZZPOGENA'.

The new Poinsettia plant is a naturally-occurring branch mutation of *Euphorbia pulcherrima* Willd. 'Allegra Art Deco', not patented. The new Poinsettia plant was discovered and selected by the Inventor on a single flowering plant from a population of plants of 'Allegra Art Deco' in a controlled greenhouse environment in Sabaudia, Italy in November, 2023.

Asexual reproduction of the new Poinsettia plant by terminal vegetative cuttings in a controlled greenhouse environment in Sabaudia, Italy since July, 2024 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'LAZZPOGENA'. These characteristics in combination distinguish 'LAZZPOGENA' as a new and distinct Poinsettia plant:

1. Upright and broad "V"-shaped and uniformly mounding plant habit.
2. Moderately vigorous growth habit.
3. Short internodes.
4. Freely branching habit and strong stems.
5. Dark green-colored leaves.
6. Full inflorescences with pale yellow and purplish pink bi-colored flower bracts.
7. Excellent post-production longevity.

Plants of the new Poinsettia can be compared to plants of the mutation parent, 'Allegra Art Deco'. Plants of the new Poinsettia differ primarily from plants of 'Allegra Art Deco' in flower bract color as flower bracts of plants of the new Poinsettia are pale yellow and purplish pink bi-colored whereas flower bracts of plants of 'Allegra Art Deco' are dark red and red bi-colored. In addition, plants of the new Poinsettia flower have shorter internodes than plants of 'Allegra Art Deco'.

Plants of the new Poinsettia can be compared to plants of *Euphorbia pulcherrima* Willd. 'Superba Marble Impr.', not patented. In side-by-side comparisons, plants of the new Poinsettia differ primarily from plants of 'Superba Marble Impr.' in the following characteristics:

1. Plants of the new Poinsettia are more broader than plants of 'Superba Marble Impr.'.
2. Plants of the new Poinsettia are less vigorous than plants of 'Superba Marble Impr.'.

3. Leaves of plants of the new Poinsettia are lobes whereas leaves of plants of 'Superba Marble Impr.' are serrate.

BRIEF DESCRIPTION OF THE PHOTOGRAPH

The accompanying photograph illustrates the overall appearance of the new Poinsettia plant showing the colors as true as it is reasonably possible to obtain in colored reproductions of this type. Colors in the photograph may differ slightly from the color values cited in the detailed botanical description which accurately describe the colors of the new Poinsettia plant. The photograph is a side perspective view of a typical flowering plant of 'LAZZPOGENA' grown in a container.

DETAILED BOTANICAL DESCRIPTION

The aforementioned photograph and following observations and measurements describe plants grown during the winter in 14-cm containers in a glass-covered greenhouse in Sabaudia, Italy and under cultural practices typical of commercial Poinsettia production. During the production of the plants, day temperatures averaged 28° C., night temperatures averaged 22° C. and light levels averaged 300 klux. Plants were pinched one time eight weeks after sticking cuttings, grown under natural daylength conditions and were six months old when the photograph and the detailed description were taken. In the following description, color references are made to The Royal Horticultural Society Colour Chart, 1995 Edition, except where general terms of ordinary dictionary significance are used.

Botanical classification: *Euphorbia pulcherrima* Willd. 'LAZZPOGENA'.

Parentage: Naturally-occurring branch mutation of *Euphorbia pulcherrima* Willd. 'Allegra Art Deco', not patented.

Propagation:

*Type*.—Terminal vegetative cuttings.

*Time to initiate roots, summer*.—About 18 days at soil temperatures ranging from 25° C. to 28° C. and ambient temperatures ranging from 30° C. to 35° C.

*Time to produce a rooted young plant, summer*.—About four weeks at soil temperatures ranging from 25° C. to 28° C. and ambient temperatures ranging from 30° C. to 35° C.

*Root description*.—Medium to fine, slightly fleshy; typically pale creamy white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Upright and broadly "V"-shaped and uniformly mounding plant habit; moderately vigorous growth habit and moderate growth rate; full inflorescences positioned above the foliar plane.

*Plant height, soil level to top of foliar plane*.—About 35 cm.

*Plant height, soil level to top of floral plane*.—About 40 cm.

*Plant diameter or spread*.—About 40 cm.

*Lateral branch description*.—Branching habit: Freely branching habit with about five to six primary lateral branches developing after pinching each with about three to four secondary lateral branches per primary lateral branch. Length: About 15 cm. Diameter: About 8 mm to 10 mm. Internode length: About 1.5 cm. Strength: Moderately strong, sturdy. Aspect, primary lateral branches: About 37° from vertical. Texture and luster: Smooth, glabrous; glossy. Color, developing: Close to 146B. Color, developed: Close to 146A; at the internodes, close to 146C.

*Leaf description*.—Arrangement: Alternate, simple. Length: About 10 cm to 12 cm. Width: About 9 cm to 10 cm. Shape: Ovate. Apex: Acuminate. Base: Cuneate. Margin: Lobed; sinuses medium in depth and parallel. Venation pattern: Pinnate, reticulate. Texture and luster, upper surface: Smooth, glabrous; glossy. Texture and luster, lower surface: Rugose, glabrous; matte. Color: Developing leaves, upper surface: Centers, close to 137C; towards the margins, close to 137A. Developing leaves, lower surface: Close to 137C. Fully expanded leaves, upper surface: Close to 139A; venation, close to 144A. Fully expanded leaves, lower surface: Close to 137B; venation, close to 144A. Petioles: Length: About 2 cm to 4 cm. Diameter: About 3 mm. Strength: Moderately strong. Texture and luster, upper and lower surfaces: Smooth, glabrous; glossy. Color, upper and lower surfaces: Close to 144A.

Inflorescence description:

*Inflorescence type and habit*.—Full inflorescences are compound corymbs of cyathia with colored flower bracts subtending the cyathia; one inflorescence per lateral branch with inflorescences positioned above and beyond the foliar plane.

*Fragrance*.—None detected.

*Natural flowering season*.—Plants flower naturally during the late autumn to winter under long nyctoperiod conditions; inflorescence initiation and development can be induced under artificial long nyctoperiod conditions; response time is about 8 to 8.5 weeks.

*Post-production longevity*.—Excellent post-production longevity; plants of the new Poinsettia maintain good substance and bract color for about four to six weeks; flower bracts persistent.

*Inflorescence diameter*.—About 20 cm to 25 cm.

*Inflorescence height*.—About 4 cm to 6 cm.

*Flower buds*.—Length: About 5 mm. Diameter: About 3 mm. Shape: Ovoid. Texture and luster: Smooth, glabrous; matte. Color: Close to 137C.

*Flower bracts*.—Quantity per inflorescence: About ten to twelve. Length: About 10 cm to 12 cm. Width: About 8 cm to 10 cm. Shape: Ovate. Apex: Acuminate. Base: Cuneate. Margin: Lobed. Aspect: Mostly horizontal to slightly drooping. Venation: Pinnate. Texture and luster, upper surface: Rugose, glabrous; matte. Texture and luster, lower surface: Moderately rugose, glabrous; matte. Color: Developing bracts, upper surface: Centers, close to 57D surrounded by close to 144A. Developing bracts, lower surface: Centers, close to 58D surrounded by close to 137B. Fully expanded bracts, upper surface: Centers, close to 58D surrounded by close to 161C to 161D and becoming closer to 162D with subsequent development. Fully expanded bracts, lower surface: Centers, close to 58D surrounded by close to 162D. Bract petioles: Length: About 2.5 cm. Diameter: About 2 mm. Texture, upper and lower surfaces: Smooth, glabrous. Color, upper and lower surfaces: Close to 47B.

*Cyathia*.—Quantity per corymb: About six to eight. Length: About 5 mm to 6 mm. Width: About 5 mm. Shape: Ovoid. Texture, inner and outer surfaces: Smooth, glabrous. Color, developing, inner and outer surfaces: Close to 12A. Color, fully developed, inner and outer surfaces: Close to 13B. Nectaries: Quantity per cyathium: Typically one. Length: About 4 mm. Diameter: About 2 mm. Shape: Lip-shaped. Texture, inner and outer surfaces: Smooth, glabrous. Color, when developing and fully developed, inner surface: Close to 13A. Color, when developing and fully developed, outer surface: Close to 13B.

*Pedicels*.—Length: About 3 mm to 5 mm. Diameter: About 1 mm. Strength: Moderately strong. Aspect: About 38° from lateral branch axis. Texture and luster: Smooth, glabrous; matte. Color: Close to 145B.

*Reproductive organs*.—Stamens: Quantity per cyathia: About five to six. Filament length: About 2 mm. Filament color: Close to 138B. Anther size: About 1 mm by 1 mm. Anther color: Close to 12A. Amount of pollen: Moderate. Pollen color: Close to 12B. Pistils: Quantity per cyathia: Typically two or three. Pistil length: About 3 mm to 4 mm. Style length: About 2 mm to 3 mm. Stigma diameter: About 0.1 mm. Stigma color: Pinkish. Ovary color: Close to 138D. Fruits: Quantity per plant: Fruits are not typically produced by plants of the new Poinsettia, however, occasionally, one or two fruits may be produced per plant. Length: About 8 mm to 10 mm. Diameter: About 5 mm to 6 mm. Texture: Smooth, glabrous. Color: Close to 145A tinged with close to 63A. Seeds: Quantity per fruit: About three to four. Length: About 0.4 mm. Diameter: About 0.3 mm. Texture: Smooth, glabrous. Color: Close to 199C.

Pathogen & pest resistance: To date, plants of the new Poinsettia have not been shown to be resistant to pathogens and pests common to Poinsettia plants.

Temperature tolerance: Plants of the new Poinsettia have been observed to tolerate temperatures from 10° C. to 39° C.

It is claimed:

1. A new and distinct Poinsettia plant named 'LAZZPOGENA' as herein illustrated and described.

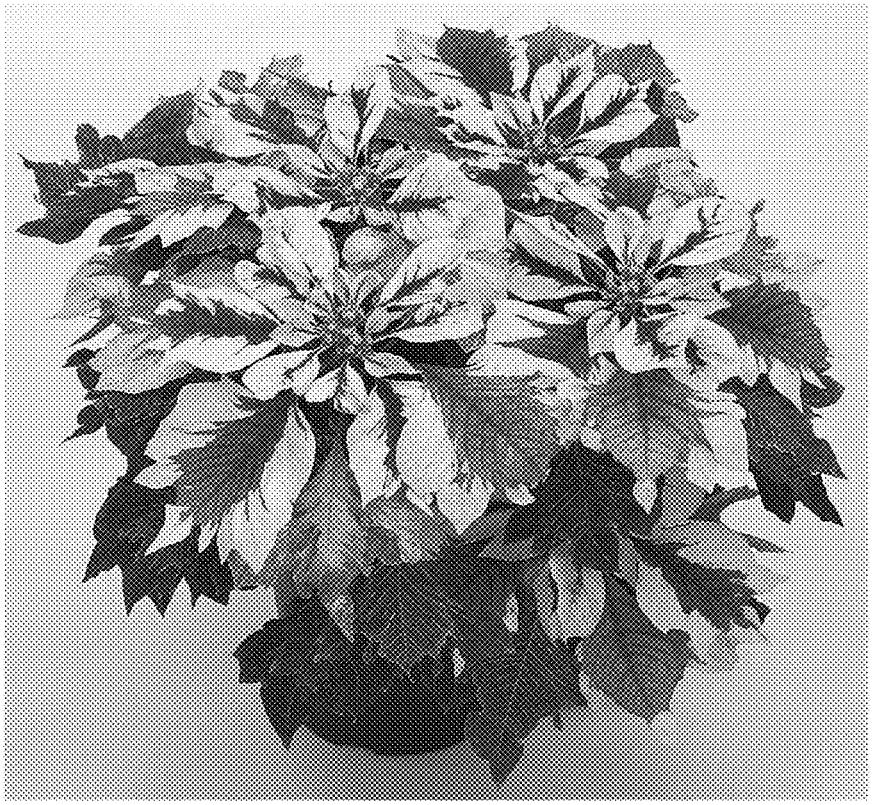

* * * * *